United States Patent [19]

Sredni et al.

[11] Patent Number: 5,271,925
[45] Date of Patent: Dec. 21, 1993

[54] METHOD FOR PROTECTING AGAINST THE EFFECTS OF RADIATION WHICH IS BASED ON THE ADMINISTRATION OF A SELENIUM OR TELLURIUM BASED COMPOUND

[76] Inventors: Benjamin Sredni, Yona Hanavi Street 22, Beni Brak; Michael Albeck, 8 Harel Street, Ramat-Gan, both of Israel

[21] Appl. No.: 846,562

[22] Filed: Mar. 5, 1992

Related U.S. Application Data

[63] Continuation of Ser. No. 491,681, Mar. 9, 1990, abandoned.

[51] Int. Cl.⁵ .................. A61K 31/335; A61K 49/00
[52] U.S. Cl. .................................. 424/10; 514/450; 514/452; 514/463; 514/917
[58] Field of Search .................. 424/10; 514/917, 450, 514/452, 463

[56] References Cited

U.S. PATENT DOCUMENTS

| | | | |
|---|---|---|---|
| 4,752,614 | 6/1988 | Albeck et al. | 514/450 |
| 4,764,461 | 8/1988 | Albeck et al. | 435/68 |
| 4,929,739 | 5/1990 | Sredni et al. | 549/347 |

OTHER PUBLICATIONS

Nat. Immun. Cell Growth Reg. 7:163-168 (1988).
J. Immunol. 140:108-11 (1988).
Experimental Hemotology 16:752-757 (1988).
Arcl Toxicol. 63:386-93 (1989).

*Primary Examiner*—Richard L. Raymond
*Assistant Examiner*—Gary E. Hollinden
*Attorney, Agent, or Firm*—Hedman, Gibson & Costigan

[57] ABSTRACT

Methods for providing radioprotection to humans and other animals employing certain organic derivatives of tellurium and selenium are disclosed.

8 Claims, 8 Drawing Sheets

METHOD FOR PROTECTING AGAINST THE EFFECTS OF RADIATION WHICH IS BASED ON THE ADMINISTRATION OF A SELENIUM OR TELLURIUM BASED COMPOUND

This is a continuation of application Ser. No. 07/491,681, filed Mar. 9, 1990, abandoned.

FIELD OF THE INVENTION

The present invention relates to a method for protecting humans and other animals from the effects of toxic doses of radiation.

BACKGROUND OF THE INVENTION

The following abbreviations are used throughout the following specification and in the claims:
IL-1=Interleukin-1
CSF=Colony Stimulating Factor
G-CSF=Granulocyte Colony Stimulating Factor
GM-CSF=Granulocyte Macrophage Colony Stimulating Factor
LPS=Bacterial Lipopolysacharide
TNF=Tumor Necrosis Factor
IFN=Interferon
BM=Bone Marrow
CFU-C=Committed Stem Cells In Albeck et al., U.S. Pat. No. 4,764,461, which is incorporated herein by reference, there are described certain organic compounds of tellurium and selenium which are active in vitro and in vivo for the production of cytokines. These compounds are described as useful in the treatment of certain tumors, autoimmune diseases, immune diseases and infectious diseases. In Albeck et al., U.S. patent application, Ser. No. 07/172,642, filed Mar. 24, 1988, which is incorporated herein by reference, there are provided complexes of certain organic tellurium and selenium compounds with non-toxic complexing agents which have increased water solubility.

Sredni et al., U.S. patent application, Ser. No. 07/302,002, filed Jan. 26, 1989, which is incorporated by reference disclosed tellurium halides which are also useful in the practise of the invention.

It is also known that a variety of inflammatory and immuno-enhancing agents administered to mice prior to irradiation increases the number of animals which survive after lethal irradiation. The increase in survival is said to be associated with an earlier recovery of mature cells in the peripheral blood and hematopoietic colony-forming cells in the bone marrow and spleen. See, Smith et al., "Effects of Bacterial Endotoxin on the Occurrence of Spleen Colonies in Irradiated Mice," Radiat. Res., 27:389, 1966; Patchen et al., "Comparative Effects of Soluble and Particulate Glucans on Survival in Irradiated Mice," J. Biol. Response Mod., 5:45, 1986; Boggs et al., "Earlier Onset of Hematopoietic Differentiation after Expansion of the Endogenous Stem Cell Pool," Radiat. Res., 63:165, 1975; and Smith et al., "Effect of Endotoxin on the Kinetics of Hemopoietic Colony-Forming Cells in Irradiated Mice," Radiat. Res., 27:710, 1969, all of which are incorporated by reference.

Protection and/or recovery from the consequences of ionizing radiation has also been investigated at different cellular and molecular levels. DNA repair mechanisms and the chemical radioprotection afforded by thiol compounds are disclosed in Elkind, "Repair Processes in Radiation Biology," Radiat. Res. 100:425, 1984 and Nygaard et al., "Radioprotectors and Anticarcinogens," Academic Press, New York, 1983, both of which are incorporated herein by reference. Radioprotection has also been reported to be conferred by immunomodulatory substances. Numerous microbial compounds such as bacterial lipopolysacharide (LPS) muramyl dipeptide, Mycobacterium bovis strain BCG, and glucan are disclosed as having radioprotective effects when administered before irradiation. Behling, U. H., "Beneficial Effects of Endotoxin," Plenum Press, New York, 1983, incorporated herein by reference. Other studies have disclosed that large molecular weight compounds such as dextran-sulfate, carbon particles and polyacrylamide beads exhibit radioprotective effects when given 1-3 days before irradiation. See, Ross et al., "Radioprotection Conferred by Dextran-Sulfate Given Before Irradiation in Mice," Exp. Hematol., 14:147, 1988; Mori et al., "Reticuloendothellal System Blockade as an Effective Method of Radioprotection," Experimentia, 31:112, 1975; and Herodin et al., "Radioprotective Effect of an Acute Non-Specific Inflammation in Mice", Int. J. Radiat. Biol. 51:549, 1987, all of which are incorporated herein by reference.

Interleukin-1 (IL-1) has also been disclosed as a radioprotector. In Neta et al., "Radioprotection with IL-1: Comparison with Other Cytokines," Prog. IMM VI:900, 1986; Neta, et al., "Interleukin 1 Is a Radioprotector," J. Immunol. 136:2483, 1986; and Swartz et al., "Recovery of Hematopoietic Colony-Forming Cells in Irradiated Mice Pretreated with Interleukin-1," Exp. Hematol., 16:752, 1988, all of which are incorporated herein by reference, the authors demonstrated that a single injection of murine or human recombinant IL-1 alpha increased survival in lethally irradiated mice. In another study, the authors demonstrated that suboptimal doses of IL-1 in combination with non-protective doses of Granulocyte Macrophage colony stimulating factor (GM-CSF), Granulocyte colony stimulating factor (G-CSF) or Tumor necrosis factor (TNF) result in synergistic protection from radiation induced death. Neta et al., "Interdependence of the Radioprotective Effects of Human Recombinant Interleukin 1-a, Tumor Necrosis Factor and Granulocyte Colony-Stimulating Factor, and Murine Recombinant Granulocyte-Macrophage Colony Stimulating Factor," J. Immunol. 140:108, 1988.

It has now been surprisingly discovered that a certain class of synthetic organic derivatives of tellurium or selenium are capable of providing radio-protection from lethal effects of irradiation and significantly diminish hematopoietic damage caused by sublethal doses of irradiation.

Accordingly, it is a primary object of this invention to provide a method for reducing hematopoietic damage caused by irradiation which is based on the use of certain organic compounds of tellurium and selenium. It is also an object of this invention to provide a method for increasing survivability from lethal doses of irradiation which is based on the use of certain organic compounds of tellurium and selenium.

SUMMARY OF THE INVENTION

According to the present invention there is provided a method for reducing hematopoietic damage caused by irradiation, the method comprising contacting hematopoietic cells prior to the irradiation with an effective amount of a compound of the formula:

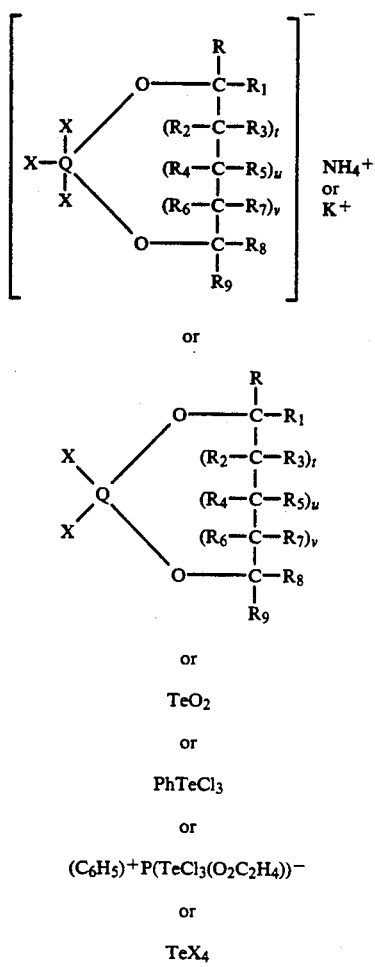

(A)

or (B)

or

TeO₂ (C)

or

PhTeCl₃ (D)

or $(C_6H_5)^+P(TeCl_3(O_2C_2H_4))^-$ (E)

or

TeX₄ (F)

wherein Q is Te or Se; t is 1 or 0; u is 1 or 0; v is 1 or 0; R, R₁, R₂, R₃, R₄, R₅, R₆, R₇, R₈ and R₉ are the same or different and are independently selected from the group consisting of hydrogen, hydroxyalkyl of 1 to 5 carbon atoms, hydroxy, alkyl of 1 to 5 carbon atoms, halogen, haloalkyl of 1 to 5 carbon atoms, carboxy, alkylcarbonylalkyl of 2 to 10 carbon atoms, alkanoyloxy of 1 to 5 carbon atoms, carboxyalkyl of 1 to 5 carbon atoms, acyl, amido, cyano, amidoalkyl of 1 to 5 carbon atoms, N-monoalkylamidoalkyl of 2 to 10 carbon atoms, N,N-dialkylamidoalkyl of 4 to 10 carbon atoms, cyanoalkyl of 1 to 5 carbon atoms, alkoxy of 1 to 5 carbon atoms, alkoxyalkyl of 2 to 10 carbon atoms, and —COR₁₀ wherein R₁₀ is alkyl of 1 to 5 carbon atoms; and X is halogen or complexes thereof.

Preferably the compound is of the formula:

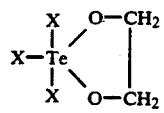

wherein X is halogen. Most preferably X is chlorine and the compound is ammonium trichloro(dioxoethylene-0,0')tellurate.

Also, according to the present invention there is provided a method for increasing the survivability of humans or animals from a lethal dose of irradiation, the method comprising administering to a human or other animal before or immediately after irradiation an effective amount of the above-defined compounds.

BRIEF DESCRIPTION OF THE DRAWINGS

FIG. 4b shows the effect of the compound AS (Example 1) on CSF secretion by bone marrow cells when AS is administered before irradiation.

DETAILED DESCRIPTION OF THE PRESENT INVENTION

Figure 1:
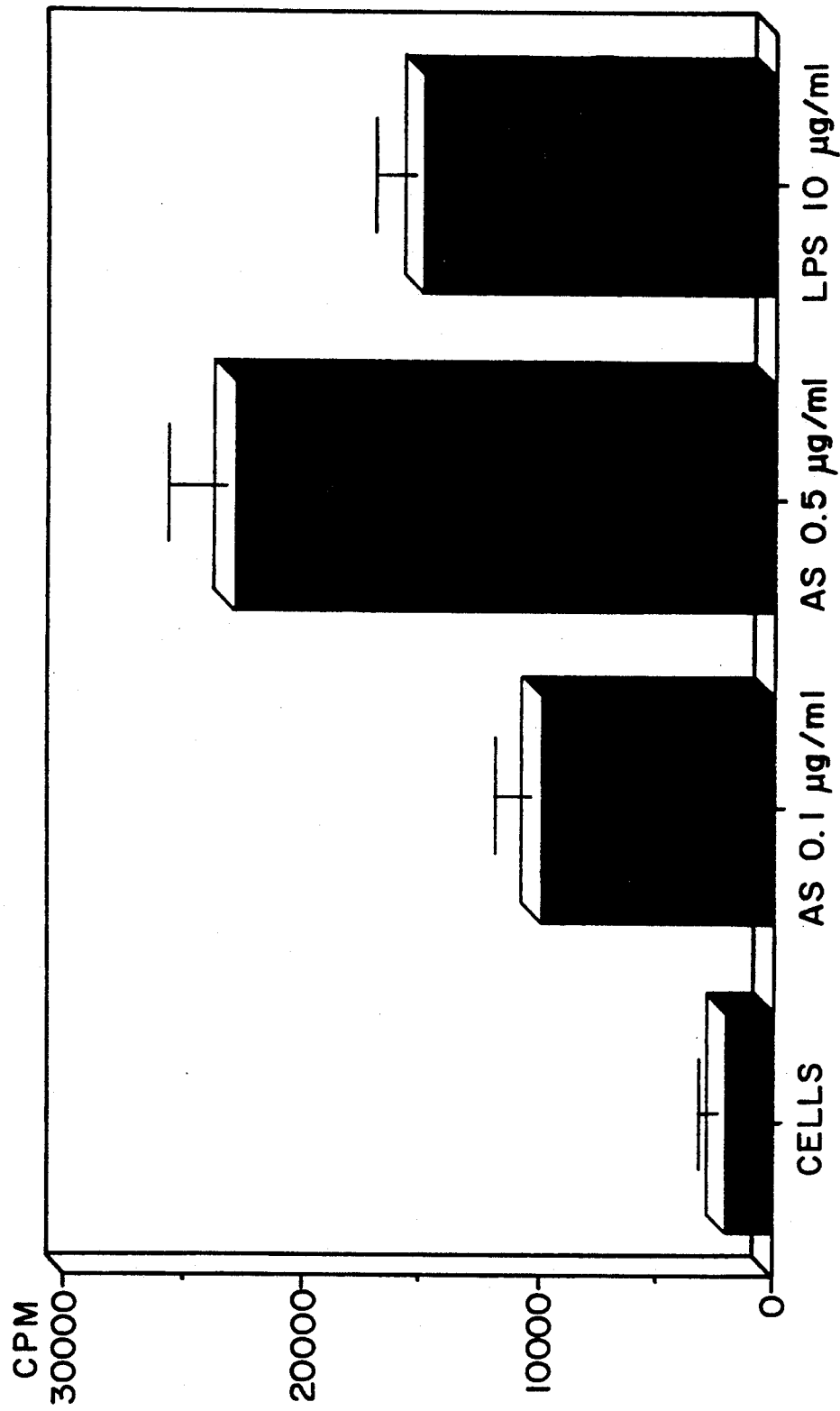
FIG. 1 demonstrates the effect of a compound of the present invention on IL-1 secretion by mouse peritoneal exudate adherent cells in vitro.

The present invention provides methods of radioprotection employing certain organic compounds of tellurium and selenium. This provides a useful tool for reducing the time needed for restoration of hemopoiesis when used in combination with irradiation in tumor therapy. The compounds useful in the practice of the present invention are generally of the following formula:

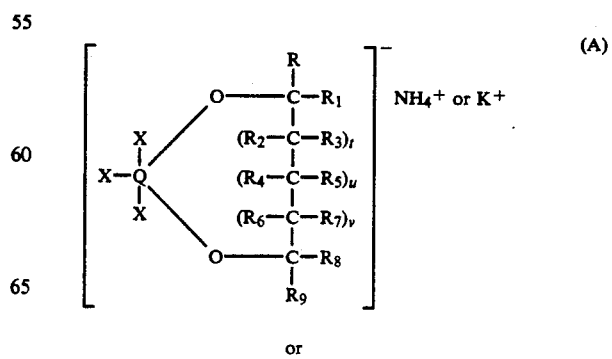

(A)

or

-continued

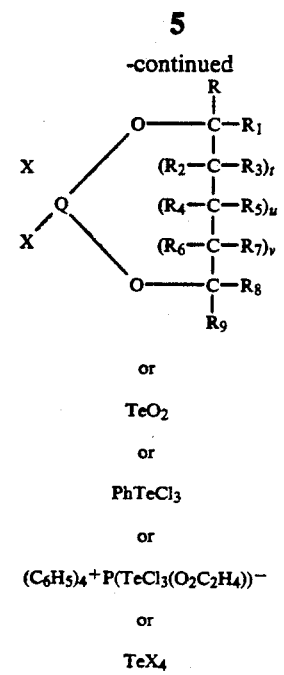

or

TeO₂ (C)

or

PhTeCl₃ (D)

or $(C_6H_5)_4^+ P(TeCl_3(O_2C_2H_4))^-$ (E)

or

TeX₄ (F)

wherein Q is Te or Se; t is 1 or 0; u is 1 or 0; v is 1 or 0; R, R₁, R₂, R₃, R₄, R₅, R₆, R₇, R₈ and R₉ are the same or different and are independently selected from the group consisting of hydrogen, hydroxyalkyl of 1 to 5 carbon atoms, hydroxy, alkyl of 1 to 5 carbon atoms, halogen, haloalkyl of 1 to 5 carbon atoms, carboxy, alkylcarbonylalkyl of 2 to 10 carbon atoms, alkanoyloxy of 1 to 5 carbon atoms, carboxyalkyl of 1 to 5 carbon atoms, acyl, amido, cyano, amidoalkyl of 1 to 5 carbon atoms, N-monoalkylamidoalkyl of 2 to 10 carbon atoms, N,N-dialkylamidoalkyl of 4 to 10 carbon atoms, cyanoalkyl of 1 to 5 carbon atoms, alkoxy of 1 to 5 carbon atoms, alkoxyalkyl of 2 to 10 carbon atoms and —COR₁₀ wherein R₁₀ is alkyl of 1 to 5 carbon atoms; and X is halogen; while the potassium and ammonium salts may be used, it is understood that other pharmaceutically acceptable salts are within the scope of the invention. The compounds with the five membered rings are preferred.

As used herein and in the appended claims, the term alkyl of 1 to 5 carbon atoms includes straight and branched chain alkyl groups such as methyl, ethyl, n-propyl, n-butyl, and the like; the term hydroxyalkyl of 1 to 5 carbon atoms includes hydroxymethyl, hydroxyethyl, hydroxy-n-butyl; the term haloalkyl of 1 to 5 carbon atoms includes chloromethyl, 2-iodoethyl, 4-bromo-n-butyl, iodoethyl, 4-bromo-n-pentyl and the like; the term alkanoyloxy of 1 to 5 carbon atoms includes acetyl, propionyl, butanoyl and the like; the term carboxyalkyl includes carboxymethyl, carboxyethyl, ethylenecarboxy and the like; the term alkylcarbonylalkyl includes methanoylmethyl, ethanoylethyl and the like; the term amidoalkyl includes —CH₂CONH₂, —CH₂CH₂CONH₂, —CH₂CH₂CH₂CONH₂ and the like; the term cyanoalkyl includes —CH₂CN, —CH₂CH₂CN, —CH₂CH₂CH₂CN and the like; the term alkoxy of 1 to 5 carbon atoms includes methoxy, ethoxy, n-propoxy, n-pentoxy and the like; the terms halo and halogen are used to signify chloro, bromo, iodo and fluoro; the term acyl includes R₁₆CO wherein R₁₆ is H, or alkyl of 1 to 5 carbon atoms such as methanoyl, ethanoyl and the like; the term aryl includes phenyl, alkylphenyl and naphthyl; the term N-monoalkylamidoalkyl includes —CH₂CH₂CONHCH₃, —CH₂CONHCH₂CH₃; the term N,N-dialkylamidoalkyl includes —CH₂CON(CH₃)₂; CH₂CH₂CON(CH₂CH₃).

Compounds which are based on tellurium are the presently preferred compounds of the invention. The tellurium based compounds that are preferred include those of the formula:

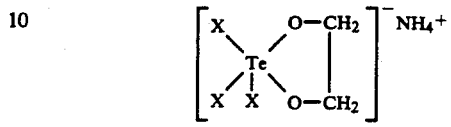

wherein X is halogen. The preferred halogen species is chloro.

Useful dihydroxy compounds for use in the preparation of compounds of structure A or B, include those of formula I wherein R, R₁, R₄ and R₅ are as shown in the Table:

TABLE $$\begin{array}{c} R \quad R_4 \\ | \quad | \\ HO-C-C-OH \\ | \quad | \\ R_1 \quad R_5 \end{array}$$ (I)

| R | R₁ | R₄ | R₅ |
|---|---|---|---|
| H | H | H | H |
| H | Cl | H | H |
| H | OCH₃ | H | H |
| H | COOCH₃ | H | H |
| H | H | CN | H |
| H | CHO | H | H |
| H | H | COOH | H |
| H | CH₂COOH | H | H |
| H | H | CHCOOCH₃ | H |
| H | I | H | H |
| H | H | Br | H |
| H | H | CONH₂ | H |
| H | H | CH₂OH | H |
| H | COOH | H | H |

Other dihydroxy compounds for use in the preparation of compounds A and B include those of formula II wherein R, R₁, R₂, R₃, R₄ and R₅ are as shown in the Table:

$$\begin{array}{c} R \quad R_2 \quad R_4 \\ | \quad | \quad | \\ HO-C-C-C-OH \\ | \quad | \quad | \\ R_1 \quad R_3 \quad R_5 \end{array}$$ (II)

| R | R₁ | R₂ | R₃ | R₄ | R₅ |
|---|---|---|---|---|---|
| H | H | H | H | H | H |
| H | H | Cl | H | H | H |
| H | CH₂OH | H | H | H | H |
| H | H | OH | H | H | H |
| H | H | H | CH₃ | H | H |
| H | H | H | CH₂Cl | H | H |
| H | H | H | COOH | H | H |
| H | H | H | CH₂COOH | H | H |
| H | H | H | CHO | H | H |
| H | H | H | H | H | CH₂CHO |
| H | H | CONH₂ | H | H₂ | CH₃ |
| H | H | H | CN | H | H |
| H | H | H | H | CH₂CONH₂ | H |
| H | H | H | COOCH₃ | H | H |
| H | H | OCH₃ | H | H | H |

Other dihydroxy compounds for use in making compounds of formula A and B include those of formula III wherein R, $R_1$, $R_2$, $R_3$, $R_4$ and $R_5$ are as shown in the Table.

$$HO-\underset{\underset{R_1}{|}}{\overset{\overset{R}{|}}{C}}-\underset{\underset{R_3}{|}}{\overset{\overset{R_2}{|}}{C}}-\underset{\underset{R_5}{|}}{\overset{\overset{R_4}{|}}{C}}-\underset{\underset{R_9}{|}}{\overset{\overset{R_8}{|}}{C}}-OH \quad (III)$$

| R | $R_1$ | $R_2$ | $R_3$ | $R_4$ | $R_5$ | $R_8$ | $R_9$ |
|---|---|---|---|---|---|---|---|
| H | H | H | H | H | H | H | H |
| H | H | Cl | H | H | H | H | H |
| H | H | H | H | Br | H | H | H |
| H | H | OCH$_3$ | H | H | H | H | H |
| H | H$_2$ | CONH$_2$ | H | H | H | H | H |
| H | Br | H | H | Br | H | H | H |
| H | H | H | H | CH$_2$COOH | H | H | H |
| H | H | Cl | Cl | H | H | H | H |
| H | CH$_2$COOH | H | H | H | H | H | H |
| H | H | CH$_3$ | H | H | H | H | H |
| H | CH$_3$ | H | H | H | H | H | H |
| H | CH$_2$Cl | H | H | H | H | H | H |
| H | H | H | I | H | H | H | H |
| H | CH$_2$CN | H | H | H | H | H | H |
| H | H | H | H | CH$_2$CH$_2$OH | H | H | H |

Additional dihydroxy compounds include those of formula IV wherein R, $R_1$, $R_2$, $R_3$, $R_4$ and $R_5$ are as shown in the Table.

unexpectedly secrete very high levels of CSF with a very small number of cells. The amount of CSF produced by BM cells is three times higher than that produced by spleen cells.

This ability of compounds of the present invention to induce the secretion of a variety of cytokines may indicate that it is able to accelerate the restoration of functional hematopoietic cells, since administration of various cytokines in vivo has been reported to stimulate a broader spectrum of progenitor cells than anticipated. For example, high doses of GM-CSF stimulated CFU-GEMM, CFU-E and BFU-E in addition to the expected myelogenous cells. See, Broxmeyer et al., "The Comparative Effects In Vivo of Recombinant Murine Interleukin-3 (IL-3), Recombinant Murine Granulocyte-Macrophage (GM) Colony Stimulating Factor (CSF) and Natural Murine (CSF-1) on Myelopolesis in Mice," J. Clin. Inves., 79:721, 1986; Metcalf, "The Molecular Biology and Function of the Granulocyte Macrophage Colony Stimulating Factors," Blood, 67:257, 1986; and Plazer et al., "Lymphokines and Monokines in the Clinic," Immunol. Today, 7:185, 1986. All of which are incorporated herein by reference.

It is known to those skilled in the art that the late S phase of a cell cycle is the most radio-resistant cell cycle phase. See, Sinclair, "Cyclic X-ray Responses in Mam- $$HO-\underset{\underset{R_1}{|}}{\overset{\overset{R}{|}}{C}}-\underset{\underset{R_3}{|}}{\overset{\overset{R_2}{|}}{C}}-\underset{\underset{R_5}{|}}{\overset{\overset{R_4}{|}}{C}}-\underset{\underset{R_7}{|}}{\overset{\overset{R_6}{|}}{C}}-\underset{\underset{R_9}{|}}{\overset{\overset{R_8}{|}}{C}}-OH \quad (IV)$$

| R | $R_1$ | $R_2$ | $R_3$ | $R_4$ | $R_5$ | $R_6$ | $R_7$ | $R_8$ | $R_9$ |
|---|---|---|---|---|---|---|---|---|---|
| H | H | H | H | H | H | H | H | H | H |
| H | H | Cl | H | H | H | Cl | H | H | H |
| H | H | Cl | Cl | H | H | H | H | H | H |
| H | H | CONCH$_3$ | H | H | H | Br | H | H | H |
| H | H | Br | H | H | H | CON(CH$_3$)$_2$ | H | H | H |
| H | H | H | OCH$_3$ | H | H | H | H | H | H |
| H | H | H | H | OCH$_3$ | H | H | H | H | H |
| H | H | H | H | CH$_2$COOH | H | H | H | H | H |
| H | H | COOH | H | H | H | H | H | H | H |
| H | CH$_3$ | H | H | H | H | H | H | H | H |
| CH$_3$ | H | H | H | H | CH$_3$ | H | H | H | H |
| H | CH$_2$CH$_3$ | H | H | H | H | H | Cl | H | H |
| H | CH$_2$CN | H | H | CH$_2$OH | H | H | H | H | H |
| H | H | H | I | H | H | H | H | CN | H |
| H | CH$_2$CH$_2$COOH | H | H | H | H | H | H | H | H |
| H | H | CHO | H | H | H | H | H | H | H |
| H | H | H | F | H | H | H | H | H | H |

The compounds of the present invention especially ammonium trichloro(dioxoethylene-0,0')-tellurate, when administered to humans and other animals, will protect humans and other animals from normally lethal doses of radiation and will significantly promote the recovery of bone marrow and spleen cells and bone marrow CFU-GM in sublethally irradiated humans and other mammals.

It is believed, although the inventors do not wish to be bound to any theory, that the ability of the compounds of the present invention to surprisingly impart radioprotection by inducing in vitro and in vivo very high levels of cytokines such as IL-1, TNF, g-INF and CSF. The secretion of IL-1 after stimulation with compounds of the present invention is more than double that obtained after stimulation with LPS. Furthermore, the compounds of the present invention have the ability to stimulate in vitro the secretion of CSF by either or both spleen or BM cells. Of particular interest, BM cells stimulated with compounds of the present invention malian Cells In Vitro," Radiat. Res., 33:620; and Denenkamp, "Cell Kinetics and Radiation Biology," Int. J. Radiat. Biol., 49:357, 1986, both of which are incorporated herein by reference. Since some cytokines, IL-1 in Neta et al., "The In Vivo Effects of Interleukin-1," J. Immunol., 139:1881, 1987 (incorporated herein by reference), and CSF in Broxmeyer et al., supra, have been reported to enhance BM cell cycling, it could be hypothesized that the compounds of the present invention have radioprotective effects by inducing the secretion of these cytokines which in turn induce large numbers of BM cells into the radioresistant S phase.

Moreover, the compunds of the present invention have previously been demonstrated to increase the intracellular Ca$^{++}$ influx into human PBL. Sredni et al., "A New Immunomodulating Compound (AS101) with Potential Therapeutic Application," Nature, 330:173, 1987, incorporated herein by reference. Further, the mechanism of stimulation by compounds of the present invention of IL-2 and CSF secretion by mouse and human cells was shown to resemble that of the calcium ionophore. Sredni et al., "Synergism Betweeen AS101 and PMA in Lymphokine Production," Immunology, 69:110, 1990 (incorporated herein by reference). CFU-S was shown, by Gallien-Lartigue, "Calcium and Ionophore A-23187 as Initiators of DNA Replication in the Pluripotent Haemopoiesis Stem Cell," Cell Tissue Kinet., 9:533, 1976 (incorporated herein by reference), to be rapidly stimulated into cell cycle in vitro by calcium ionophore A-23187 and other conditions that increased the intracellular influx of $Ca^{++}$. Thus, after injections of compounds of the present invention, intracellular $Ca^{++}$ levels may be increased sufficiently to initiate DNA sysnthesis of non-cycling populations of CFU-S and thus afford radioprotection. After irradiation, a greater number of CFU-S will survive and permit the reconstitution of hemopoiesis.

The compounds of the invention should be administered to the human or other animal prior to irradiation in an amount which is effective for diminishing the hematopoietic damage after sublethal irradiation or for increasing the rate of survival after lethal irradiation. The compounds are also effective when administered immediately after exposure to radiation, i.e. up to 30–60 minutes. This activity makes the invention of special utility to workers in the nuclear industry and to the military where personnel may be exposed to radiation.

The compounds of the present invention may be administered orally, parenterally, transcutaneously, topically or by contacting mucuous membranes. The compounds may be administered orally in hard or soft gel liquid capsules, in solutions or suspension capsules or tablets that may be prepared using conventional excipients, binders, disintegrating agents and the like. The parenteral route may be intramuscular, intravenous, intradermal using a sustained release carrier or subcutaneous. The concentration of the compounds in combination with a pharmaceutical carrier is not critical and is a matter of choice. Remington's Practice of Pharmacy, 9th, 15th or 16th Ed. describes various pharmaceutical carriers and is incorporated herein by reference.

It has been found that a number of the tellurium compounds useful in the practice of the invention will hydrolyze in the presence of water. These hydrolyzed compositions are active in vivo and in vitro although the hydrolyzed compositions eventually decompose and lose their radioprotection ability. For this reason, the compositions should be freshly prepared. If the compounds are administered orally in dry form, they are active in radioprotection. Preferably, the compounds should be kept under anhydrous conditions until just prior to being used.

Topical compositions may be prepared by dispersing the compounds in a hydrophillic or hydrophobic cosmetic base. Petroleum jelly or commercial preparations such as Oil of Olay may be used. The concentration may be from 0.0001–5% on a weight/weight basis.

The dosage of the compounds of the invention used to effect radioprotection may be varied depending on the particular dose of irradiation. Generally an amount of the compound may be administered which will range from $0.05 \times 10^{-3}$ to $1 \times 10^{-3}$ g/Kg of body weight and preferably from $0.1 \times 10^{-3}$ to $0.5 \times 10^{-3}$ g/Kg of body weight. For example a dosage of 1-3 mg per day for a 75 kg mammal is contemplated as a sufficient amount to induce radioprotection but the dosage may be adjusted according to the individual response and the particular condition that is being treated.

For in vitro use, cells may be stimulated to produce lymphokines by use of $1 \times 10^{-8}$ to $1 \times 10^{-4}$, preferably $1 \times 10^{-7}$ to $1 \times 10^{-5}$ g of compound per $10^6$ cells/ml.

DESCRIPTION OF THE PREFERRED EMBODIMENTS

The following examples are given to illustrate the present invention and it is understood that they do not limit the scope of the invention.

I. MATERIALS AND METHODS

A. MICE

Balb/c male mice, 2 months of age were purchased from Jackson Laboratories, Bar Harbor, Me., and housed 10 mice per cage.

B. TREATMENT WITH AMMONIUM TRICHOLORO(DIOXOETHYLENE-0,0')TELLURATE

Ammonium trichloro(dioxoethylene-0,0')tellurate was administered to mice at concentrations ranging from 2.5 to 40 μg/0.2 ml/injection. The compound was supplied in a solution of phosphate buffer saline at pH 7.4 and maintained at 4° C. Before use, the compound was diluted in PBS and the appropriate concentrations in 0.2 ml volume were administered to normal mice every other day by intraperitoneal injections two weeks before, or following, irradiation. Control mice were administered 0.2 ml PBS at the same time. Hematological monitoring was concluded 9 days after irradiation.

C. RECOVERY OF BONE MARROW (BM) AND SPLEEN CELLS

Femurs and spleens were removed and placed in PBS solution. Single cell suspensions of BM were prepared by washing each cavity of the femur with 5 ml PBS with a sterile syringe and 26-gauge needle. Spleen cells were passed through stainless steel mesh nets, treated with hypotonic solution to lyse erythrocytes and washed 3 times. Cell counts were obtained using a hemocytometer. Viability, as assessed by the trypan blue exclusion method, was always found to be greater than 95 percent.

D. CSF PRODUCTION

Spleen cells, $5 \times 10^6$/ml, or BM cells, $5 \times 10^5$/ml, were suspended in enriched RPMI 1640 medium with 10 percent FCS and supplemented with 0.5 ug/ml ammonium trichloro(dioxoethylene-0,0')tellurate and 20 ng/ml PMA. Spleen cell cultures were incubated for 24 hours and BM cells were incubated for 48 hours. Supernatants were collected and assayed for CSF activity.

E. ASSAY FOR CSF ACTIVITY

CSF was quantitated by determining the number of colonies that developed from BM cells cloned in the presence of the CSF-containing fraction to be tested. The soft agar technique described by Pluznik and Sachs, "The induction of colonies of normal mast cells by a substance in conditioned medium," Exp. Cell. Res. 43:553 (1966), and incorporated herein by reference, was used to clone BM cells. Briefly, supernatants containing CSF were incorporated in 2 ml of hard medium in a 35 mm Petri dish. $10^5$ BM cells in 1 ml of soft agar medium (0.3 percent) were cloned above the hard agar layer. After seven days of incubation at 37° C. in a humidified atmosphere of 8.5 percent $CO_2$ in air, the number of colonies that had grown in the soft agar was scored.

F. QUANTITATION OF CFU-C

BM from treated mice were seeded in agar cultures as described above in the presence of rat spleen cell conditioned medium as a source of colony stimulating activity. Seven days later, colonies of more than 50 cells were scored as CFU-C.

G. PRODUCTION OF IL-1 IN VITRO

Balb/c mice were injected intraperitoneally with 1.5 ml of 0.3 percent thioglycolate. Three days later, peritoneal extrudate cells were collected and cultured at a concentration of $3 \times 10^6$/ml enriched RPMI for one hour. Non-adherent cells were collected with the supernatant and adherent cells were cultured in enriched RPMI with various concentrations of ammonium tricholoro(dioxoethylene-0,0')tellurate for six hours. Supernatants were collected and tested for IL-1 content.

H. IL-1 ASSAY 100 l of a suspension of $5 \times 10^6$/ml C3H/HeJ thymocytes in RPMI-1640 plus 10 percent FCS were added to each well of a 96-well microtiter plate containing 100 $\mu$l of serial twofold dilutions of the test supernatant or media alone. PHA at a concentration of 50 $\mu$g/ml was added to each well. Each dilution was plated in triplicate. The plates were incubated for 72 hours at 37° C. The cultures were then harvested and counted in a scintillation counter.

I. RADIATION

Mice were exposed to gamma irradiation and received total body irradiation from a Cesium-137 radiation source at a dose rate of 500 rads/min.

J. STATISTICAL ANALYSIS

The Dunnet procedure, Dunnet, "A multiple comparison procedure for comparing several treatments with controls," J. Am. Stat. Assoc., 50:1096 (1955), and incorporated herein by reference, is used for comparisons of mean values of the different ammonium trichloro(dioxoethylene-0,0')tellurate concentrations versus PBS. Proportions were compared using the Chi-Square test and survival curves were compared employing the Gehan-Wilcoxon test.

EXAMPLE 1

The induction of IL-1 production in vitro by ammonium trichloro(dioxoethylene-0,0')tellurate (AS).

The capability of ammonium trichloro(dioxoethylene-0,0')tellurate to induce IL-1 production was tested according to procedure G above. The secretion of IL-1 was analyzed in peritoneal exudate cells from mice injected with thioglycolate. FIG. 1 shows that ammonium trichloro(dioxoethylene-0,0')tellurate, at 0.5 $\mu$g/ml induced the secretion in vivo of very large amounts of IL-1. At this concentration, IL-1 secretion was more than double of that obtained after stimulation with LPS. At 0.1 $\mu$g/ml, similar amounts of IL-1 were secreted as those at 10 $\mu$g/ml LPS (FIG. 1). The LPS contamination of the substance was established by a Limulus assay and shown to contain less than 2 U per ml in the IL-1 preparation.

EXAMPLE 2

Ammonium trichloro(dioxoethylene-0,0')tellurate induction of CSF secretion in vitro by BM and spleen cells.

Figure 2:
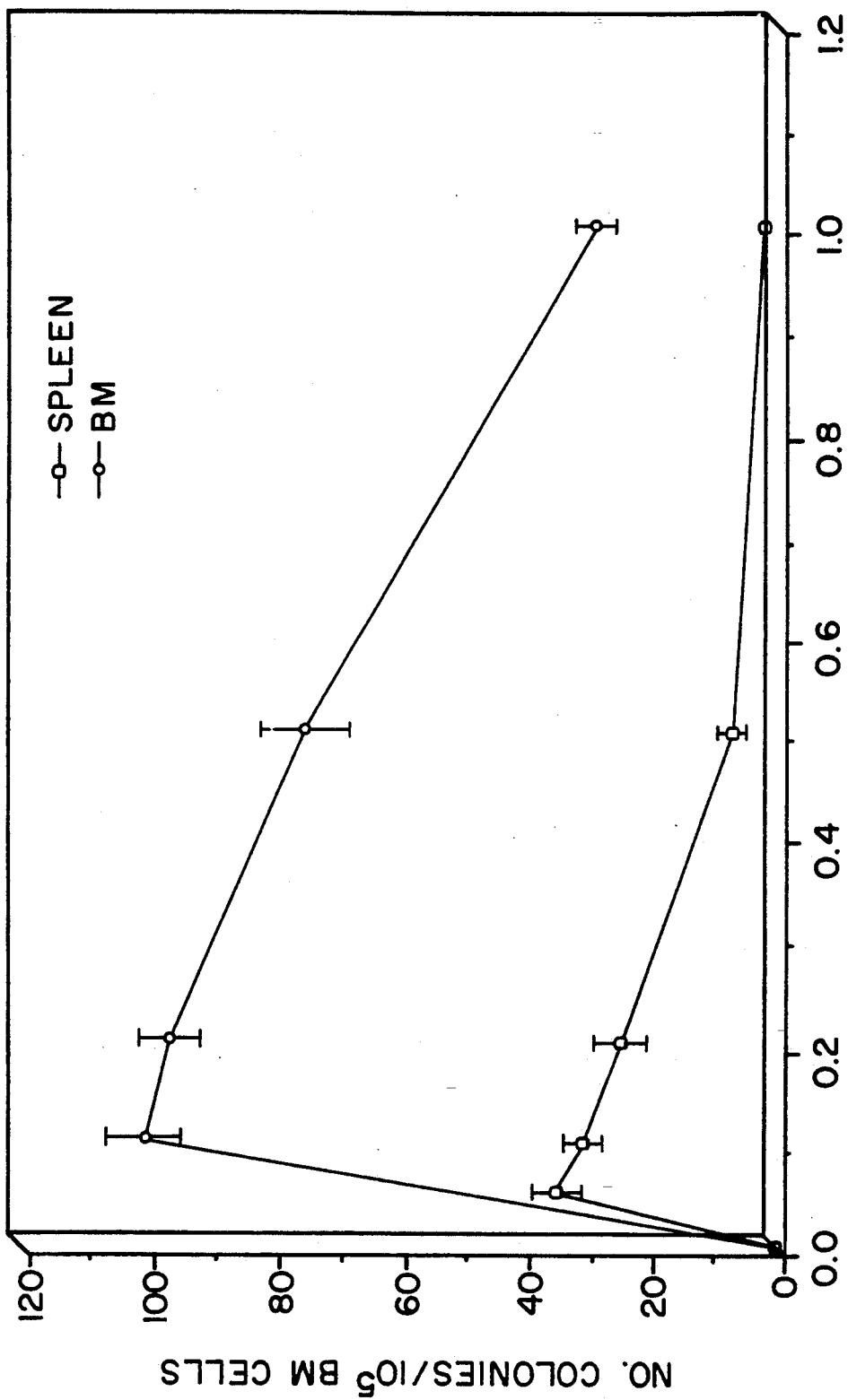
FIG. 2 demonstrates the effect of a compound of the present invention on CSF secretion in vitro by mouse bone marrow and spleen cells.

CSF secretion is induced in vitro in BM and spleen cells by varying concentrations of ammonium trichloro(dioxoethylene-0,0')tellurate according to procedure D above. As can be seen in FIG. 2, much higher levels of CSF are secreted by BM cells than by spleen cells. The levels of CSF secreted by half a million BM cells are three times higher (100±6 vs. 34±3.2) than the levels secreted by $5 \times 10^6$ spleen cells/ml.

EXAMPLE 3

Effect of ammonium trichloro(dioxoethylene-0,0')tellurate on BM and spleen cellularity.

Figure 3A:
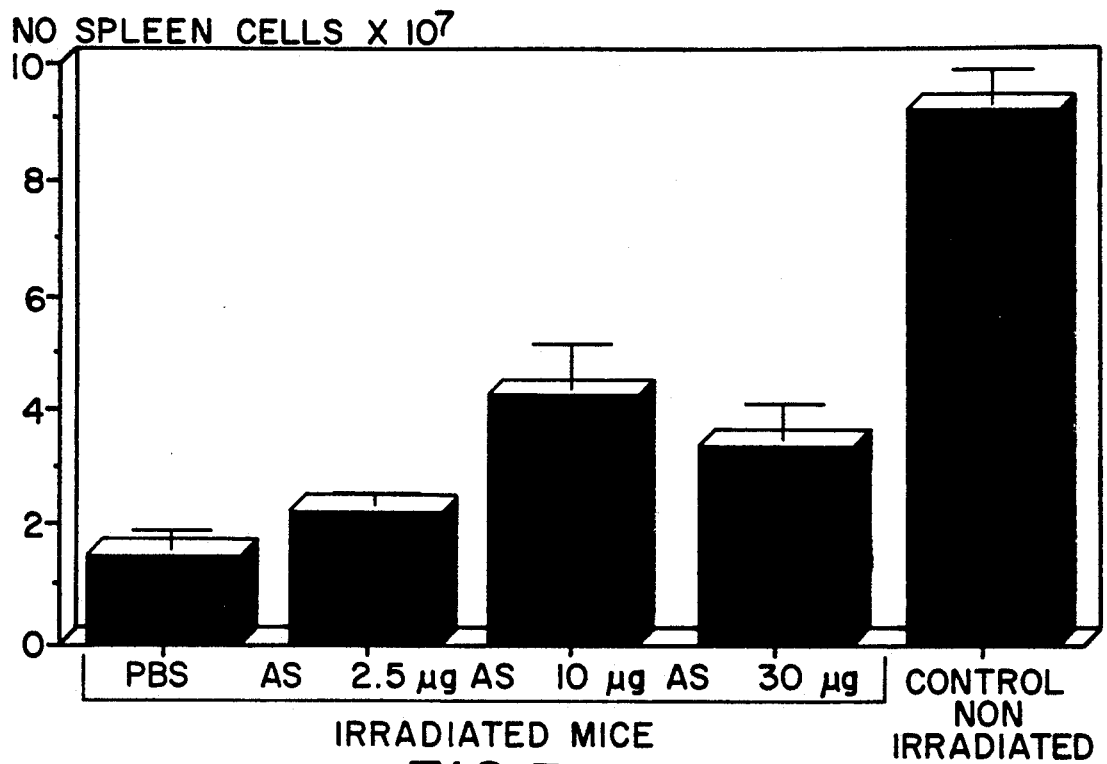
FIG. 3a shows the effect of the compound AS (Example 1) on spleen cells when AS is administered before irradiation.
Figure 3B:
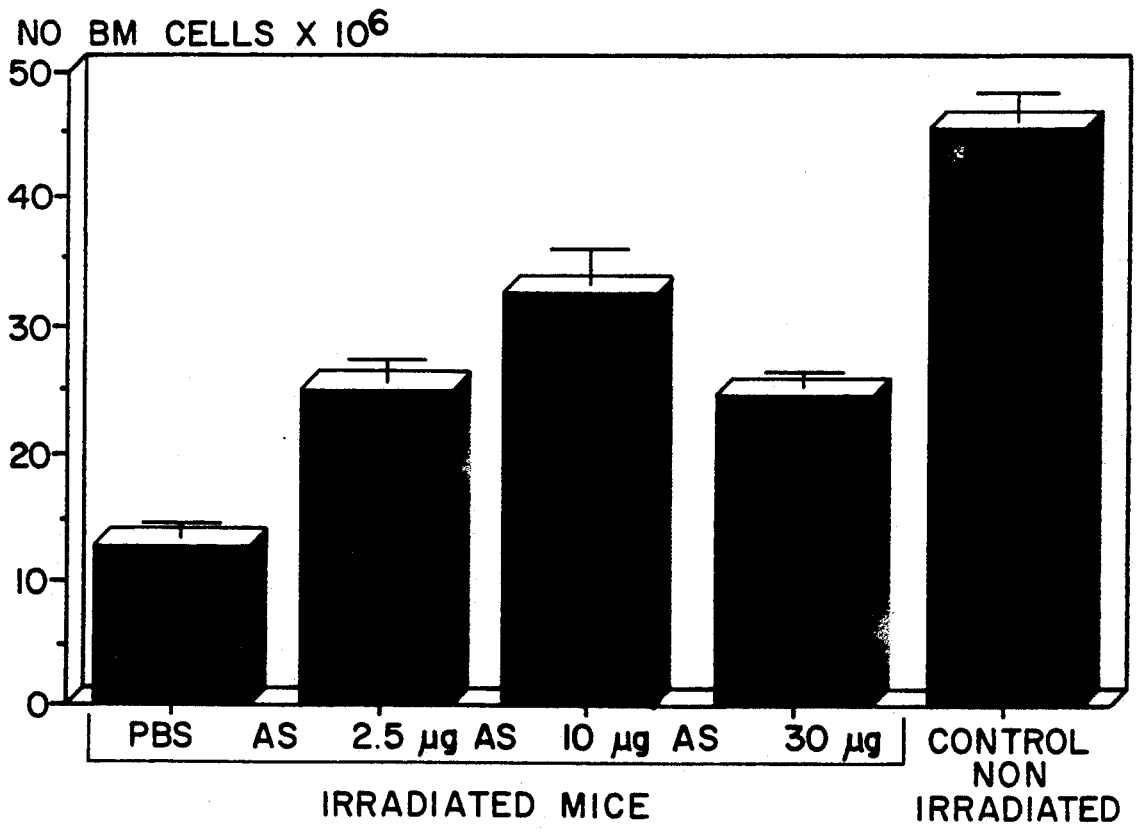
FIG. 3b shows the effect of the compound AS (Example 1) on bone marrow cells when AS is administered before irradiation.

BM and spleen cells are subjected to sublethal doses of irradiation according to procedure I above. FIG. 3 shows that there is an earlier recovery of spleen and BM cellularity in mice injected with ammonium trichloro(-dioxoethylene-0,0')tellurate before irradiation. Nine days after 450 rads irradiation, the number of spleen cells in PBS mice was less than 20 percent of normal and the number of BM cells was 30 percent of normal non-irradiated mice. These values increased threefold in spleens and BM of mice injected with ammonium trichloro(dioxoethylene-0,0')tellurate and reached almost those of normal non-irradiated mice. However, the number of spleen cells nine days after irradiation, despite having increased threefold, was only 50 percent of control non-irradiated mice.

At 10 $\mu$g/mouse injection of ammonium trichloro(dioxoethylene-0,0')tellurate, the number of BM cells increased from 12.8±1.05 to 32.65±2.7×$10^6$/2 femurs (p 0.05) and the number of spleen cells increased from 1.49±0.26 to 4.33±0.77×$10^7$/2 spleens (p<0.05). However, at a dose of 2.5 g/mouse, significant increases were noted only in BM cells (p<0.05) (FIG. 3ab).

When ammonium trichloro(dioxoethylene-0,0')-tellurate was injected after irradiation, no significant differences were noted in either dosage concentration use.

EXAMPLE 4

Effect of ammonium trichloro(dioxoethylene-0,0')tellurate on CSF secretion.

Figure 4A:
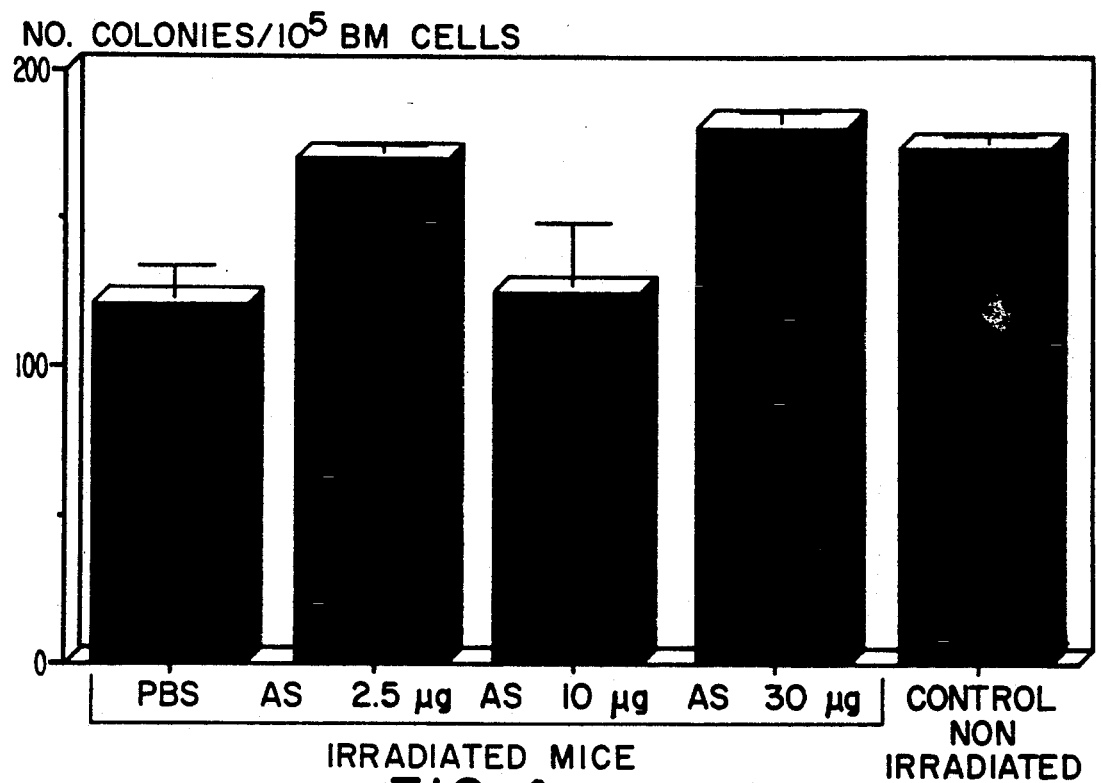
FIG. 4a shows the effect of the compound AS (Example 1) on CSF secretion by spleen cells when AS is administered before irradiation.
Figure 4B:
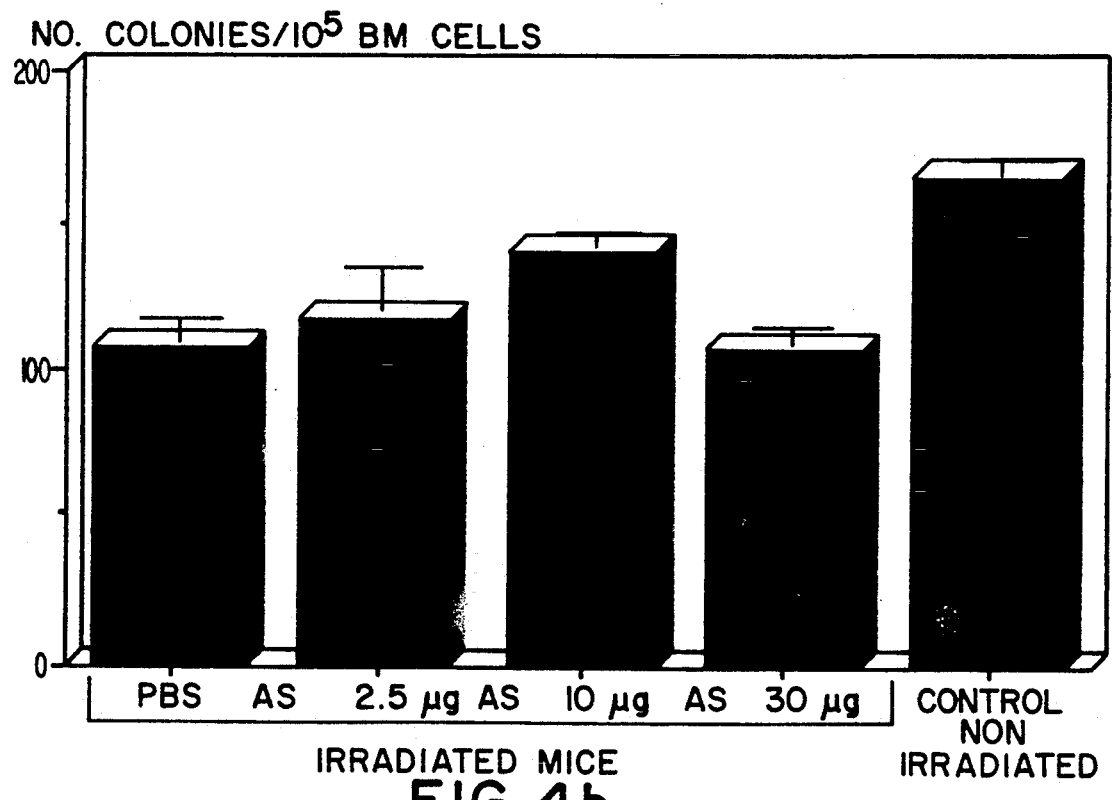
FIG. 4b shows the effect of the compound AS (Example 1) on CSF secretion by bone cells when AS is administered before irradiation.

Nine days after 450 rads irradiation, a decrease in CSF secretion by either spleen or BM cells in PBS injected mice was noted. CSF secretion amounted to 60 percent of control non-irradiated mice. See, FIG. 4ab.

However, continuous injections of ammonium trichloro(dioxoethylene-0,0')tellurate for two weeks prior to irradiation was found to almost completely prevent the decrease in CSF production by both BM and spleen cells. At a dosage of 10 ug/mouse, CSF secretion in BM cells increased from 107.9±66.7 to 141.3±3.8 colonies/$10^5$ BM cells (p<0.05); and at a dosage of 30 ug/mouse CSF secretion by spleen cells increased from 120.5±1 colonies/$10^5$ BM cells (p<0.05). See, FIG. 4ab.

Figure 5A:
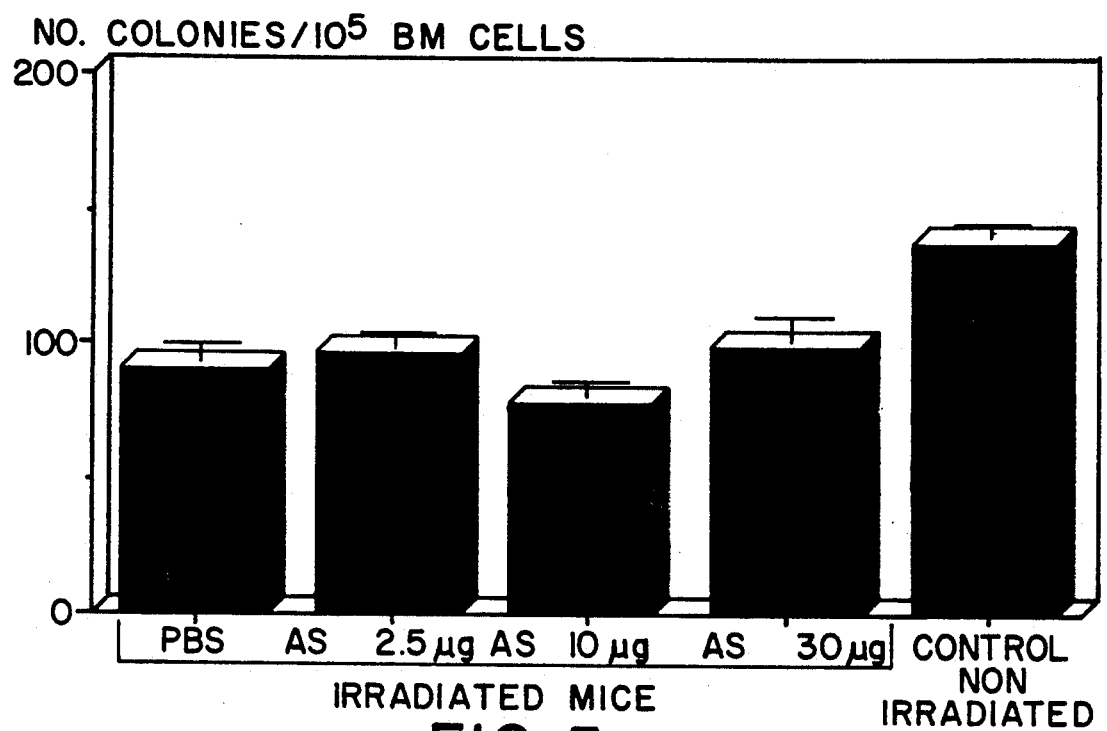
FIG. 5a shows the effect of the compound AS (Example 1) on CSF secretion by spleen cells when AS is administered after irradiation.
Figure 5B:
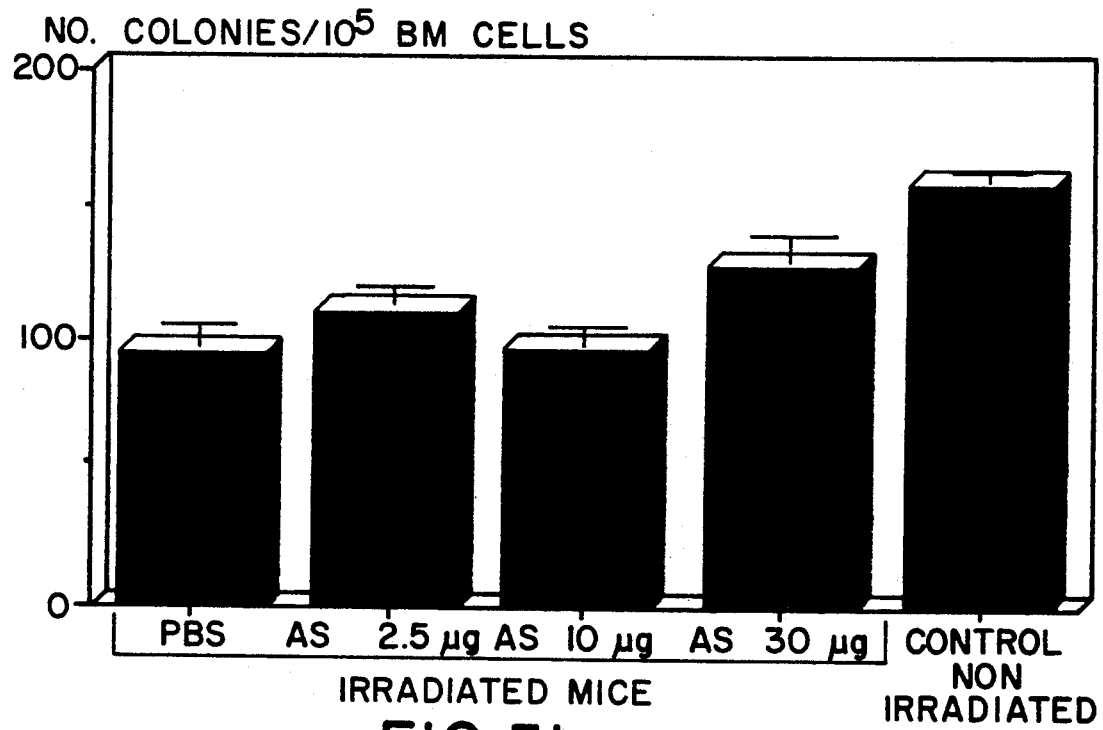
FIG. 5b shows the effect of the compound AS (Example 1) on CSF secretion by bone marrow cells when AS is administered after irradiation.

When ammonium trichloro(dioxoethylene-0,0')-tellurate was injected after irradiation, no statistically significant differences were noted in the secretion of CSF by either spleen or BM cells between PBS and ammonium trichloro(dioxoethylene-0,0')tellurate injected mice. See, FIG. 5ab.

EXAMPLE 5

Effect of ammonium trichloro(dioxoethylene-0,0')tellurate early recovery of GM-CFC after sublethal irradiation.

Figure 6:
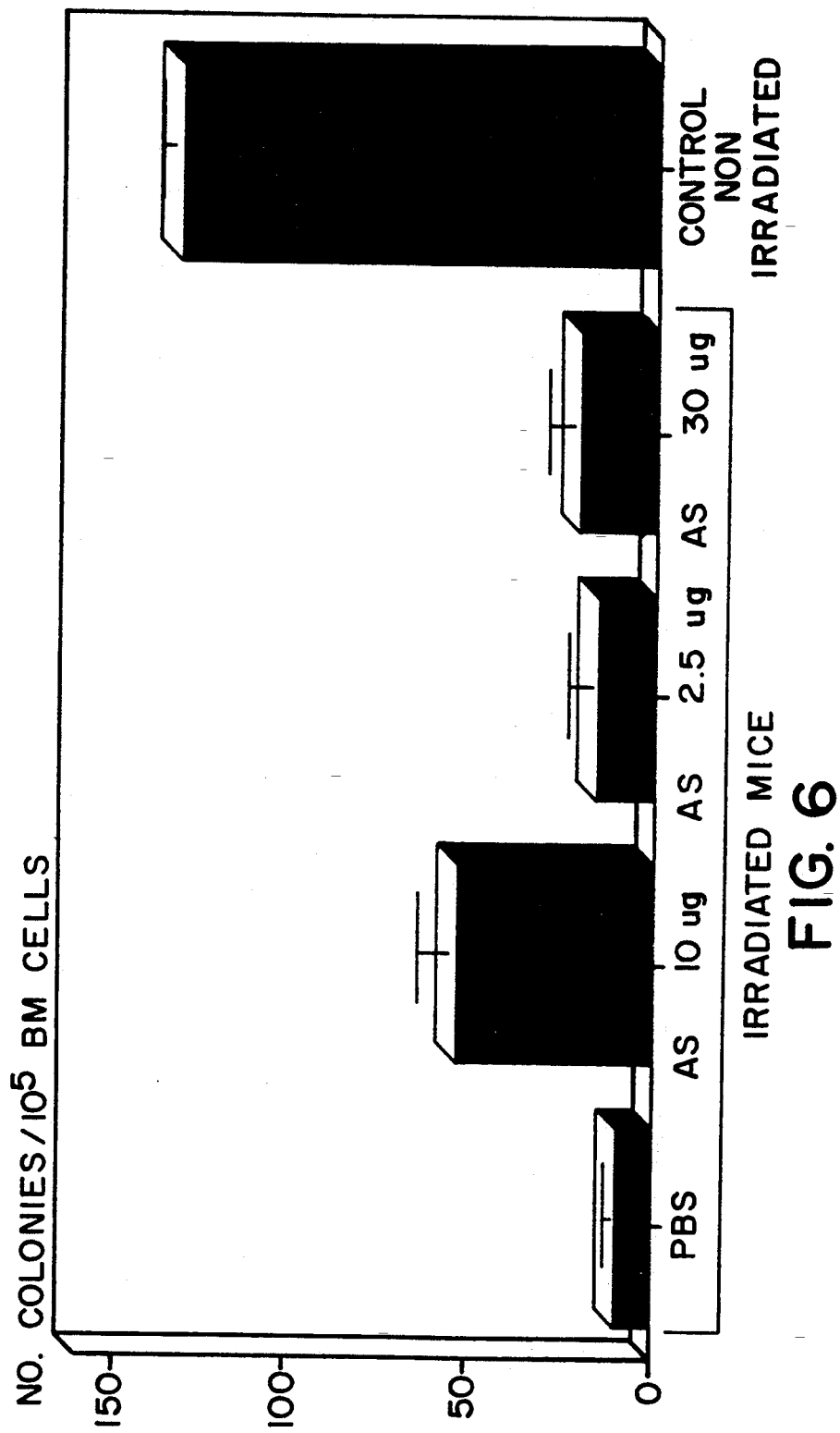
FIG. 6 demonstrates the effect of injections of a compound of the present invention before irradiation on the number of CFU-C in mouse bone marrow.

After 450 rads irradiation, 100 percent of both PBS and ammonium trichloro(dioxoethylene-0,0')-tellurate injected mice survived beyond 60 days. However, 9 days after irradiation, the number of BM-CFU-C was very low in PBS injected mice ($9.3 \pm 1$ compared to $140 \pm 4$ in control non-irradiated). Injections of 10 μg ammonium tricloro(dioxoethylene-0,0')tellurate to mice prior to irradiation brought about a marked recovery of GM-CFC (increase from $9.3 \pm 1$ in PBS injected mice to $54.1 \pm 8.4$ in ammonium trichloro(dioxoethylene-0,0')tellurate injected mice; $p<0.05$). See, FIG. 6. Continuous injections of any of the concentrations of ammonium trichloro(dioxoethylene-0,0')tellurate from day 1 to day 8 after irradiation did not change the number of CFC in the BM of irradiated mice.

The results above clearly demonstrate that ammonium trichloro(dioxoethylene-0,0')tellurate can induce the production of IL-1 and CSF in vitro and that injections of ammonium trichloro(dioxoethylene-0,0')-tellurate prior to irradiation accelerate hematopoietic recovery in sublethally irradiated mice.

EXAMPLE 6

Survival of lethally irradiated mice pretreated with ammonium trichloro(dioxoethylene-0,0')-tellurate.

Figure 7:
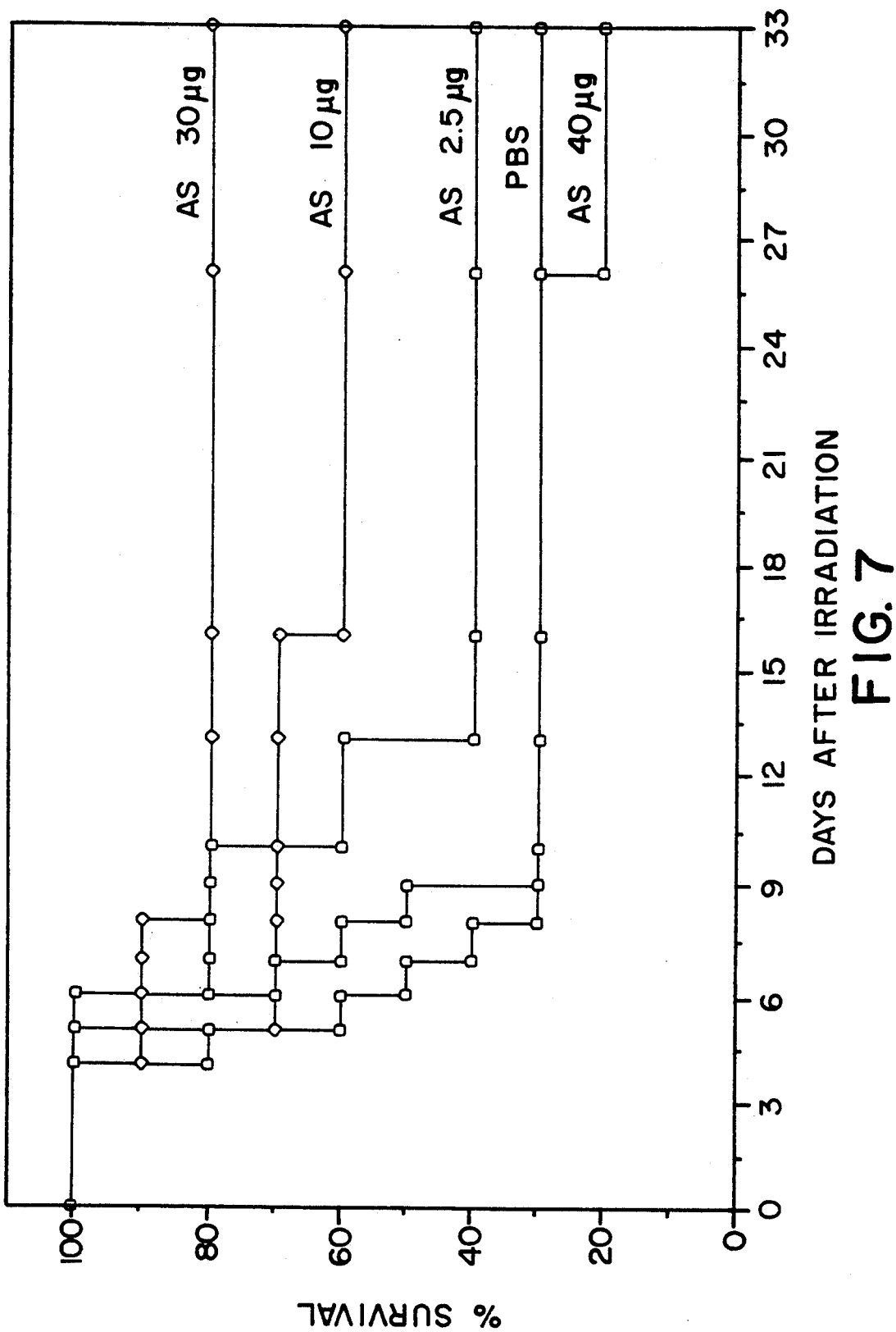
FIG. 7 demonstrates the radioprotective effect of a compound of the present invention on lethally irradiated mice.

FIG. 7 shows the percentage of survival of mice 33 days after lethal irradiation of 840 rads. Mice which were injected with varying concentrations of ammonium trichloro(dioxoethylene-0,0')tellurate two weeks prior to irradiation, every other day, displayed a dose response curve in their percentage of survival. An increase in the percentage of surviving mice was observed with an increase in dosage concentrations from 2.5 μg (40 percent survival vs. 30 percent survival) to 10 μg (83.3 percent survival vs. 30 percent survival; $p=0.021$) to 30 μg/mouse (80 percent vs. 30 percent; $p=0.001$). At a dosage of 40 μg/injection a decrease in the percentage of survival beyond that of PBS injected mice was noted (20 percent vs. 30 percent in PBS injected mice).

Figure 8:
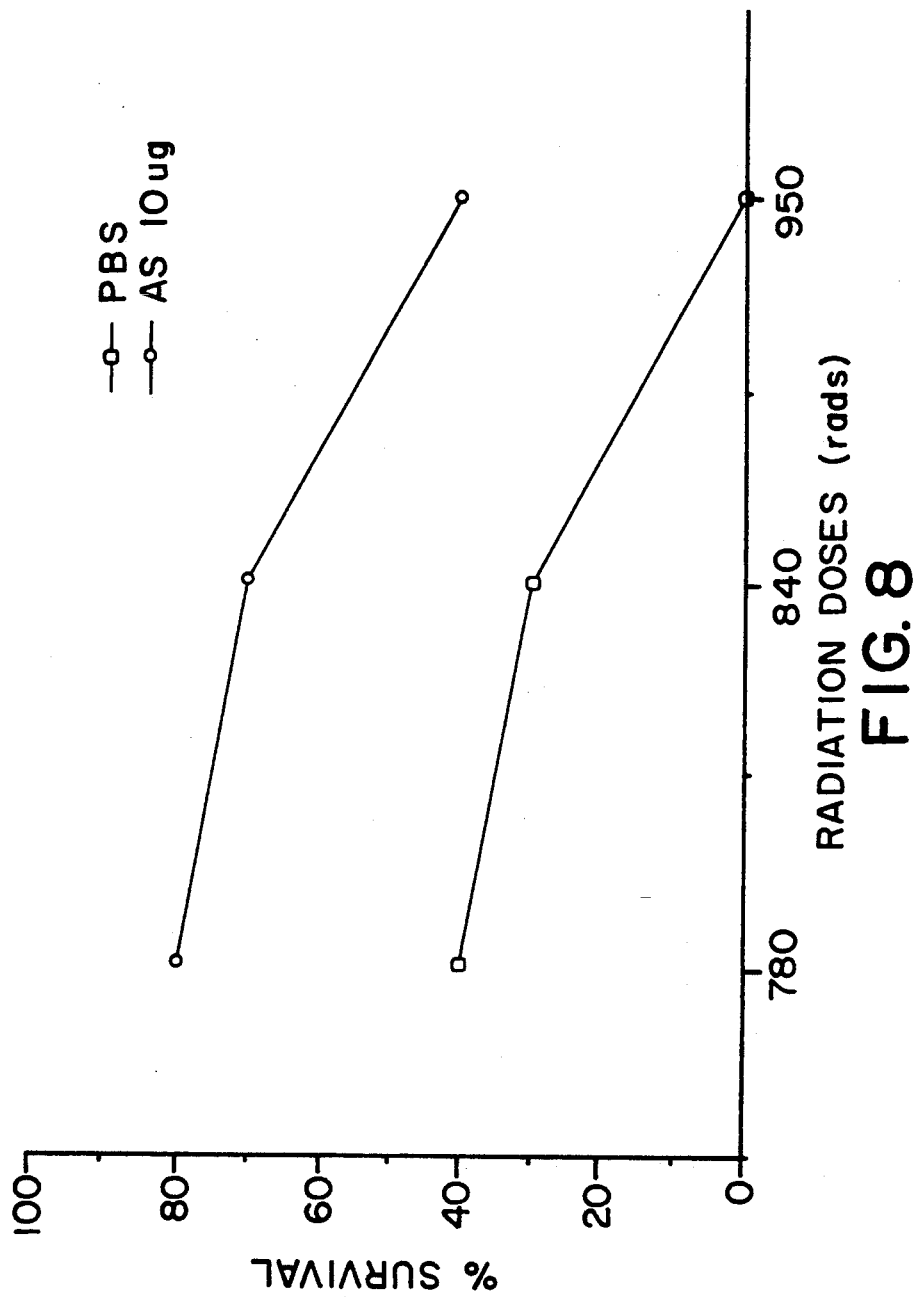
FIG. 8 demonstrates the radioprotective effect of a compound of the present invention on mice exposed to various doses of whole body irradiation.

Mice given ammonium trichloro(dioxoethylene-0,0')tellurate from day one after irradiation every second day did not increase the percentage of survival. FIG. 8 shows the percentage of survival of mice on day 30 receiving 10 μg/injection of ammonium trichloro(dioxoethylene-0,0')tellurate, two weeks prior to treatment at various irradiation doses. A significant increase in survival, 0 percent to 40 percent ($p<0.002$) at 950 rads, from 30 percent to 70 percent ($p<0.01$) at 840 rads, and from 40 percent to 80 percent ($p<0.01$) at 780 rads, is observed.

The above patents, patent applications and publications are hereby incorporated by reference.

Many variations of the present invention will suggest themselves to those skilled in the art in light of the above-detailed description. For example, a compound other than ammonium trichloro(dioxoethylene-0,0')tellurate may be employed. All such obvious modifications are within the full intended scope of the appended claims.

We claim:

1. A method for reducing hematopoietic damage cause by irradiation, said method comprising administering to a patient in need thereof prior to said irradiation, a therapeutically effective amount of a compound of the formula:

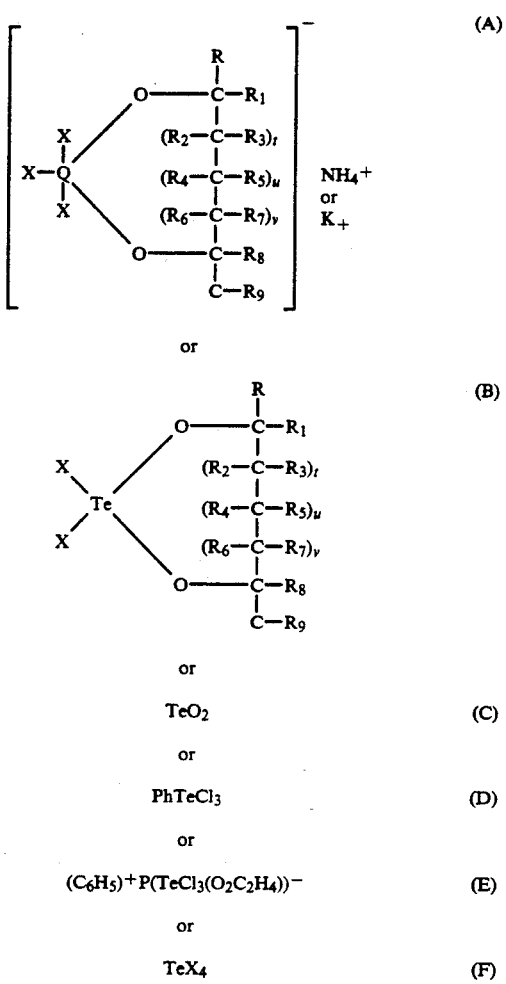

wherein Q is Te or Se; t is 1 or 0; u is 1 or 0; v is 1 or 0; R, $R_1$, $R_2$, $R_3$, $R_4$, $R_5$, $R_6$, $R_7$, $R_8$ and $R_9$ are the same or different and are independently selected from the group consisting of hydrogen, hydroxyalkyl of 1 to 5 carbon atoms, hydroxy, alkyl of from 1 to 5 carbon atoms, halogen, haloalkyl or 1 to 5 carbon atoms, carboxy, aklylcarbonylalkyl of 2 to 10 carbon atoms, alkanoyloxy of 1 to 5 carbon atoms, carboxyalkyl of 1 to 5 carbon atoms, acyl, amido, cyano, amidoalkyl of 1 to 5 carbon atoms, N-monoalkylamidoalkyl of 2 to 10 carbon atoms, N,N-dialkylamidoalkyl of 4 to 10 carbon atoms, cyanoalkyl of 1 to 5 carbon atoms, alkoxy of 1 to 5 carbon atoms, alkoxyalkyl of 2 to 20 carbon atoms and —$COR_{10}$ wherein $R_{10}$ is alkyl of 1 to 5 carbon atoms; and X is halogen or complexes thereof.

2. A method for reducing hematopoietic damage caused by irradiation as defined in claim 1 wherein said compound is of the formula:

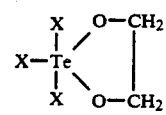

wherein X is halogen.

3. A method for reducing hematopoietic damage caused by irradiation as defined in claim 2 wherein X is chloro.

4. A method for reducing hematopoietic damage caused by irradiation as defined in claim 1 wherein said irradiation is a sublethal dose.

5. A method for increasing survivability of warm blooded animals from a lethal dose of irradiation, said method comprising administering to said warm blooded animal before or after said lethal dose of irradiation therapeutically effective amount of a compound of the formula:

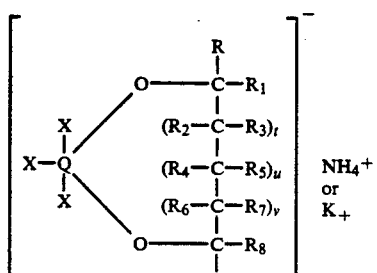
(A)

or

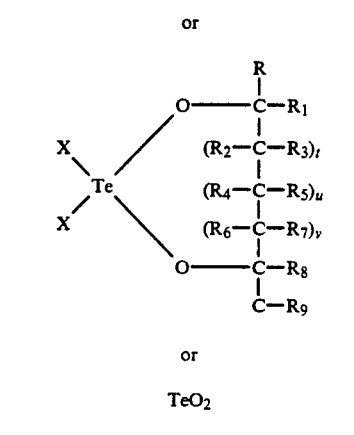
(B)

or

TeO$_2$ (C)

or

PhTeCl$_3$ (D)

or $(C_6H_5)^+P(TeCl_3(O_2C_2H_4))^-$ (E)

or

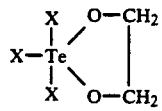
TeX$_4$ (F)

wherein Q is Te or Se; t is 1 or 0; u is 1 or 0; v is 1 or 0; R, R$_1$, R$_2$, R$_3$, R$_4$, R$_5$, R$_6$, R$_7$, R$_8$ and R$_9$ are the same or different and are independently selected from the group consisting of hydrogen, hydroxyalkyl of 1 to 5 carbon atoms, hydroxy, alkyl of from 1 to 5 carbon atoms, halogen, haloalkyl of 1 to 5 carbon atoms, carboxy, alkylcarbonylalkyl of 2 to 10 carbon atoms, alkanoyloxy of 1 to 5 carbon atoms, carboxyalkyl of 1 to 5 carbon atoms, acyl, amido, cyano, amidoalkyl of 1 to 5 carbon atoms, N-monoalkylamidoalkyl of 2 to 10 carbon atoms, N,N-dialkylamidoalkyl of 4 to 10 carbon atoms, cyanoalkyl of 1 to 5 carbon atoms, alkoxy of 1 to 5 carbon atoms, alkoxyalkyl of 2 to 20 carbon atoms and —COR$_{10}$ wherein R$_{10}$ is alkyl of 1 to 5 carbons atoms; and X is halogen or complexes thereof.

6. A method for increasing survivability of humans or other animals from a lethal dose of irradiation as defined in claim 5 wherein said compound is of the formula:

$$\begin{array}{c} X \quad O-CH_2 \\ | \diagup \quad | \\ X-Te \quad | \\ | \diagdown \quad | \\ X \quad O-CH_2 \end{array}$$

wherein X is halogen.

7. A method for increasing survivability of humans or other animals from a lethal dose of irradiation as defined in claim 6 wherein X is chlorine.

8. A method for increasing survivability of humans or other animals from a lethal dose of irradiation as defined in claim 5 wherein said compound is administered to said human or other animal immediately after said lethal dose of irradiation.

* * * * *